United States Patent [19]
Prasad et al.

[11] Patent Number: 5,856,499
[45] Date of Patent: Jan. 5, 1999

[54] SYNTHESIS OF 2-(METHYSULFONYL)-5-(TRIFLUORO-METHYL)-,3,4-THIADIAZOLE VIA OXIDATION OF 2-(METHYLTHIO)-5-(TRIFLUOROMETHYL)-1,3,4-THIADIAZOLE WITH GLACIAL ACETIC ACID

[75] Inventors: Vidyanatha A. Prasad, Lewwood, Kans.; Jacqueline M. Applegate, Pittsburgh, Pa.; Klaus Jelich, Pittsburgh, Pa.; Achim Noack, Pittsburgh, Pa.

[73] Assignees: Bayer Corporation, Pittsburgh, Pa.; Bayer Aktiengesellschaft, Leverkusen, Germany

[21] Appl. No.: 989,594

[22] Filed: Dec. 12, 1997

[51] Int. Cl.$^6$ ............................................. C07D 285/125
[52] U.S. Cl. ............................................. 548/136
[58] Field of Search ............................................. 548/136

[56] References Cited

U.S. PATENT DOCUMENTS 3,562,284  2/1971  Newman et al. ........................ 260/302
5,147,443  9/1992  Diehr ........................................ 548/136

OTHER PUBLICATIONS

Weygand Preparative Organic Chemistry pp. 667–668, 1972.

Durst T., in Comprehensive Organic Chemistry Chapter 11.6 Barton and Ollis, Eds., Pergammon Press, Oxford, (month unavailable) 1979.

*Primary Examiner*—Robert Gerstl
*Attorney, Agent, or Firm*—Joseph C. Gil; Carol Marmo

[57] ABSTRACT

The present invention provides a process for making thiadiazole sulfones. The present process is used to make 2-(methylsulfonyl)-5-(trifluoromethyl)-1,3,4-thiadiazole. 2-(Methylsulfonyl)-5-(trifluoromethyl)-1,3,4-thiadiazole is made using catalytic oxidation in the presence of a suitable oxidizing agent. The catalyst used for the oxidation reaction is glacial acetic acid.

10 Claims, No Drawings

SYNTHESIS OF 2-(METHYSULFONYL)-5-(TRIFLUORO-METHYL)-,3,4-THIADIAZOLE VIA OXIDATION OF 2-(METHYLTHIO)-5-(TRIFLUOROMETHYL)-1,3,4-THIADIAZOLE WITH GLACIAL ACETIC ACID

TECHNICAL FIELD OF THE INVENTION

The field of the present invention is the synthesis of thiadiazole sulfones. More particularly, the present invention pertains to the synthesis of 2-(methylsulfonyl)-5-(trifluoromethyl)-1,3,4-thiadiazole via a catalytic oxidation.

BACKGROUND OF THE INVENTION

Sulfones have the general structure RR'SO$_2$. Sulfones can be produced from a variety of precursors. By way of example, sulfones can be prepared by (a) oxidizing sulphides, (b) rearranging sulphinate esters, (c) adding sulfonyl halides to alkenes and acetylenes, (d) adding sulphinic acids to polarized bonds, and (e) adding SO$_2$ to polyenes (See. e.g., Durst, T., in *Comprehensive Organic Chemistry:* Chapter 11.6, Barton and Ollis, Eds., Pergammon Press, Oxford, 1979).

A particular class of sulfones, 2-(alkylsulfonyl)-5-(trifluoromethyl)-1,3,4-thiadiazoles are intermediates used in the production of herbicides. 2-(methylsulfonyl)-5-(trifluoromethyl)-1,3,4-thiadiazole has been reported to possess antifungal activity (See, U.S. Pat. No. 3,562,284). According to U.S. Pat. No. 3,562,284, 2-(substituted sulfonyl)-5-(trifluoromethyl)-1,3,4-thiadiazoles can be made by oxidizing a corresponding 2-(substituted thio)-5-(trifluoromethyl)-1,3,4-thiadiazole in the presence of an oxidizing agent such as potassium permanganate, hydrogen peroxide or peroxytrifluoroacetic acid. Oxidation takes place in an acidic, aqueous medium that includes acetic acid and methylene chloride as a solvent. Methylene chloride is an undesirable solvent from the standpoint of industrial hygiene and handling. Handling is difficult due to its low boiling point (high vapor pressure). In addition, it contaminates aqueous streams. The sulfone product is isolated using crystallization. The reported yield of the sulfone, based on the starting sulfide, was about 65%.

The use of acetic acid in the presence of water in the process necessarily introduces excess water into the reaction and requires purification of the sulfone using expensive crystallization procedures with resultant low yields. There continues to be a need in the art for a practical, inexpensive process for preparing thiadiazole sulfones in high yield.

BRIEF SUMMARY OF INVENTION

The present invention provides a process for making 2-(methylsulfonyl)-5-(trifluoromethyl)-1,3,4-thiadiazole comprising oxidizing 2-(methylthio)-5-(trifluoromethyl)-1,3,4-thiadiazole in a reaction mixture containing glacial acetic acid to form a reaction product. A preferred oxidizing agent is hydrogen peroxide. In accordance with this embodiment, the 2-(methylthio)-5-(trifluoromethyl)-1,3,4-thiadiazole is reacted with hydrogen peroxide in the presence of glacial acetic acid.

The hydrogen peroxide used in the reaction mixture is preferably an aqueous solution containing from about 30 weight percent to about 50 weight percent hydrogen peroxide. The hydrogen peroxide is present in a molar excess relative to the 2-(methylthio)-5-(trifluoromethyl)-1,3,4-thiadiazole. Preferably, the molar ratio of hydrogen peroxide to 2-(methylthio)-5-(trifluoromethyl)-1,3,4-thiadiazole is from about 2.0:1 to about 4.0:1. Even more preferably, the molar ratio is from about 2.1:1 to about 2.5:1. The glacial acetic acid is present in an amount of from about 0.5 moles to about 3.0 moles of acetic acid per mole of 2-(methylthio)-5-(trifluoro-methyl)-1,3,4-thiadiazole. More preferably, the molar ratio of glacial acetic acid to 2-(methylthio)-5-(trifluoromethyl)-1,3,4-thiadiazole is from about 0.5:1 to about 1:1. Oxidation typically occurs at a temperature of from about 60° C. to about 100° C. and, preferably at a temperature of from about 70° C. to about 90° C.

The process of-the present invention can include additional steps. Water can be removed from the reaction product. The removal of water is preferably accomplished azeotropically. Still further, a process of this invention can include the step of isolating the formed 2-(methylsulfonyl)-5-(trifluoromethyl)-1,3,4-thiadiazole.

DETAILED DESCRIPTION OF THE INVENTION

I. The Invention

The present invention provides a process for producing thiadiazole sulfones. The present process is used to make 2-(methylsulfonyl)-5-(trifluoromethyl)-1,3,4-thiadiazole (TDA sulfone) from 2-(methylthio)-5-(trifluoromethyl)-1,3,4-thiadiazole (TDA). TDA sulfone is made using catalytic oxidation of TDA in the presence of a suitable oxidizing agent. The catalyst used for the oxidation reaction is glacial acetic acid. This approach avoids the use of metal catalyst. Acetic acid is biodegradable and its disposal does not pose a problem.

II. Process for Producing TDA Sulfone Using Glacial Acetic Acid

In accordance with this aspect, the present process includes the step of oxidizing 2-(methylthio)-5-(trifluoromethyl)-1,3,4-thiadiazole (TDA) in a reaction mixture containing an activated glacial acetic acid catalyst to form a reaction product that contains the TDA sulfone. Oxidation of TDA takes place in the presence of a suitable oxidizing agent. Exemplary such oxidation agents are well know in the art (See, e.g., Durst, T., in *Comprehensive Organic Chemistry:* Chapter 11.6, Barton and Ollis, Eds., Pergammon Press, Oxford, 1979). A particularly preferred oxidizing agent is hydrogen peroxide (H$_2$O$_2$). In accordance with this embodiment, TDA is reacted with hydrogen peroxide in the presence of a catalyst. The hydrogen peroxide used in the reaction mixture is preferably an aqueous solution containing from about 30 weight percent to about 50 weight percent hydrogen peroxide. The molar ratio of H$_2$O$_2$ to TDA is from about 2:1 to about 4:1 and, preferably, about 2.2:1. Oxidation conditions are well known in the art. Typically, oxidation is carried out at a temperature of from about 60° C. to about 100° C.

TDA used in the present process can be obtained from any source. Preferably, the TDA is made by a process that provides TDA in an aprotic, aromatic solvent such as toluene. Especially preferred means for making TDA can be found in the U.S. patent applications entitled "A Process for Making 2-(Methylthio)-5-(Trifluoromethyl)-1,3,4-Thiadiazole Using Methyldithiocarbazinate and an Excess of Trifluoroacetic Acid", "A Process for Making 2-(Methylthio)-5-(Trifluoromethyl)-1,3,4-Thiadiazole using Methyidithiocarbazinate with Trifluoroacetic Acid with Removal of Bis-byproduct", and "A Process for Preparing 2-(Methylthio)-5-(Trifluoromethyl)-1,3,4-Thiadiazole Using Methyidithiocarbazinate and an Excess of Trifluoroacetic Acid With Recovery of Trifluoroacetic Acid", filed concurrently herewith. The disclosures of all three applications are incorporated herein by reference.

The oxidation of TDA occurs in the presence of a solvent. Preferably, the solvent is an aprotic, aromatic solvent. Such solvents are well known in the art. Exemplary and preferred such solvents are toluene, xylene, cumene and mesitylene. Toluene is especially preferred. The amount of solvent used can vary over a wide range as readily determined by a skilled artisan. The precise amount of solvent will depend on the particular solvent used. Where toluene is the solvent, it is present in an amount of about 0.5 moles to about 3.5 moles of toluene per mole of TDA. Preferably, toluene is present in an amount of from about 1.0 moles to about 2.0 moles per mole of TDA and, more preferably in an amount of from about 1.0 to about 1.5 moles of toluene per mole of TDA.

TDA is oxidized in a reaction mixture containing glacial acetic acid to form a reaction product that contains TDA sulfone. Sources of TDA, use of a solvent, oxidation conditions and choice of suitable oxidizing agents are the same as set forth above. Here, the oxidizing agent (e.g., hydrogen peroxide) used in the reaction mixture is preferably present in a molar excess relative to the TDA. Preferably, the molar ratio of oxidizing agent to TDA is from about 2.0:1 to about 4.0:1. Even more preferably, that ratio is from about 2.1:1 to about 2.5:1. The glacial acetic acid catalyst is directly added to the reaction mixture. Glacial acetic acid is present in an amount of from about 0.5 moles to about 1.0 moles of acetic acid per mole of TDA.

Further, water can be removed from the reaction product. Still further, a process of this invention can include the step of isolating the formed sulfone.

Water removal is preferably accomplished azeotropically. The azeotropic removal of water is readily accomplished in the presence of the solvent, particularly where the solvent is toluene. Because the azeotrope has a lower boiling point than water, heating the reaction product to the boiling point of the solvent effectively removes the water. Because the oxidation reaction occurs in the range of about 60° C. to about 100° C., water is removed during that reaction; no additional step is required.

The following Examples illustrate preferred embodiments of the present invention and are not limiting of the specification and claims in any way.

EXAMPLES

Example 1: Synthesis of TDA Sulfone Using Glacial Acetic Acid

TDA in toluene and glacial acetic acid were charged to a reaction vessel. The mixture was heated. Stabilized 35% $H_2O_2$ was added over a period of time. The resulting mixture was heated for about 4 to 6.5 hours with azeotropic removal of water. The mixture was purged with $N_2$ during the reaction. Reaction conditions were as follows:

| | |
|---|---|
| TDA/Toluene, wt. % TDA | 58–61 |
| Acetic Acid/TDA mole ratio | 0.50–0.75 |
| $H_2O_2$ add time, hrs | 3.0–4.5 |
| Reaction temp, °C. | 83–91 |
| Cook time, hrs | 4.0–6.5 |

Initial reactions were made with normal (non-stabilized) 35% $H_2O_2$. The resulting yields were less than 85%. The phases were separated at 70° C.

The TDA sulfone/toluene phase was retained for subsequent use. The phase separations were all very good, with very little interfacial rag. The average yield for the acetic acid process, using stabilized 35% $H_2O_2$ was about 95.0%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making 2-(methylsulfonyl)-5-(trifluoromethyl)-1,3,4-thiadiazole comprising oxidizing 2-(methylthio)-5-(trifluoromethyl)-1,3,4-thiadiazole in a reaction mixture containing glacial acetic acid and an oxidizing agent to form a reaction product, wherein the molar ratio of glacial acetic acid to 2-(methylthio)-5-(trifluoromethyl)-1,3,4-thiadiazole is from about 0.5:1 to about 1:1.

2. The process of claim 1 wherein the oxidizing agent is hydrogen peroxide.

3. The process of claim 1 wherein the 2-(methylthio)-5-(trifluoromethyl)-1,3,4-thiadiazole is dissolved in an aprotic, aromatic solvent.

4. The process of claim 3 wherein the solvent is toluene.

5. The process of claim 1 wherein oxidation occurs at a temperature of from about 60° C. to about 100° C.

6. The process of claim 5 wherein the temperature is from about 70° C. to about 90° C.

7. The process of claim 2 wherein the molar ratio of hydrogen peroxide to 2-(methylthio)-5-(trifluoromethyl)-1,3,4-thiadiazole is from about 2.0:1 to about 4.0:1.

8. The process of the claim 7 wherein the molar ratio of hydrogen peroxide to 2-(methylthio)-5-(trifluoromethyl)-1,3,4 thiadiazole is from about 2.1:1 to about 2.5:1.

9. The process of claim 1 further comprising azeotropically removing water from the reaction product.

10. The process of claim 1 further comprising isolating the formed 2-(methylsulfonyl)-5-(trifluoromethyl)-1,3,4-thiadiazole.

* * * * *